United States Patent [19]

Griffin

[11] 4,073,185
[45] Feb. 14, 1978

[54] TEST PIECE GRIPPING DEVICE

[76] Inventor: Alvin G. Griffin, 1006 Old Gate Road, Pittsburgh, Pa. 15235

[21] Appl. No.: 738,640

[22] Filed: Nov. 3, 1976

[51] Int. Cl.$^2$ ............................................. G01N 3/04
[52] U.S. Cl. ................................................... 73/103
[58] Field of Search .......................... 73/103, 95, 95.5

[56] References Cited

U.S. PATENT DOCUMENTS

| 3,403,549 | 10/1968 | Griffin | 73/103 |
| 3,715,916 | 2/1973 | Stickney | 73/103 |

*Primary Examiner*—Anthony V. Ciarlante
*Attorney, Agent, or Firm*—Thomas H. Murray

[57] ABSTRACT

The housing of a test piece gripping device is rectangular and includes two raised pad surfaces extending across the width of the housing at different locations. One of the raised pad surfaces extends across the housing at its upper front face while the second raised pad extends across the back of the housing. The planes of the raised pad surfaces are parallel with the plane of the associated housing faces. A faceplate is recessed in the housing to form a flush relation with its front face. The faceplate includes a continuous longitudinal slot to both guide a control member used to move cams within cam surfaces formed in gripper jaws and to expose part of the jaws for visual observation during the gripping of a test piece.

8 Claims, 4 Drawing Figures

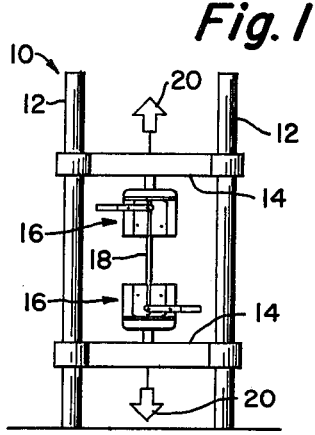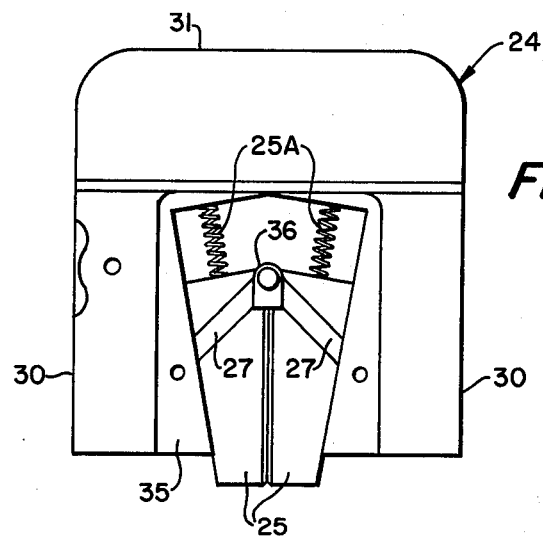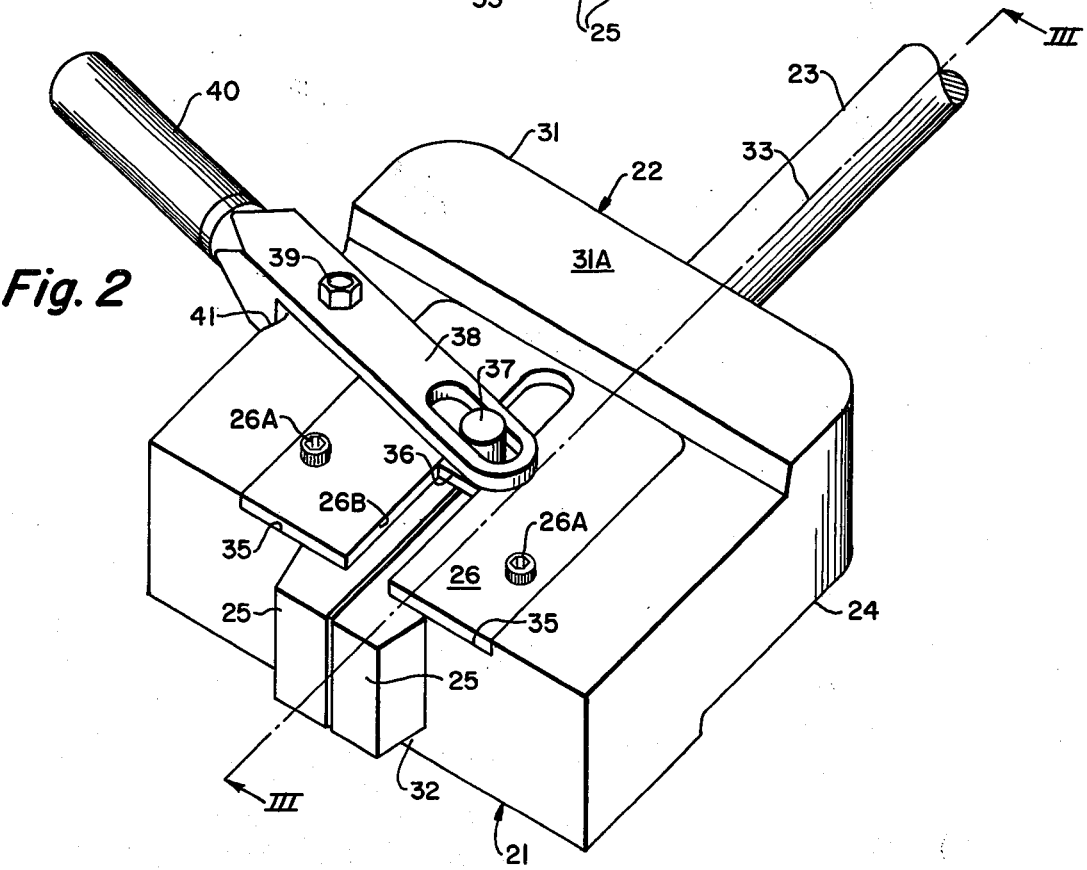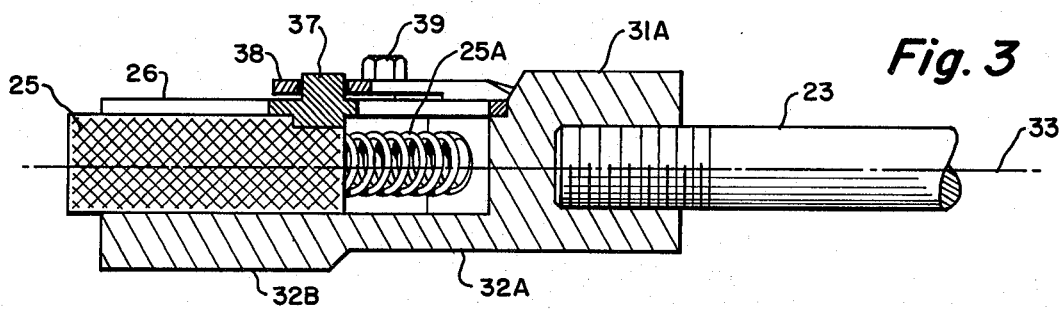

1

TEST PIECE GRIPPING DEVICE

BACKGROUND OF THE INVENTION

This invention relates to an improved construction of a housing and parts attached thereto to form a test piece gripping device, and more particularly to improvements in gripping devices of the type used in conjunction with physical testing apparatus for gripping the opposite ends of a test specimen undergoing a pull test.

As is known, gripping devices of the type described are used in conjunction with physical testing apparatus wherein two of the gripping devices are used to grip the opposite ends of a test specimen. The gripping devices are forced apart by the power components of the physical testing apparatus to subject the test specimen to various tensile forces. Among the physical properties of the test specimen, which are to be determined in this manner, are yield strength, ultimate strength and breaking stress. As is known in the art and specifically, for example, as shown in my prior U.S. Pat. No. 3,403,549, such gripping devices each consists of a housing having oppositely-inclined side walls. A jaw member is engaged with and slideable over each of the inclined walls. The inclination of the side walls is such that the jaw members are moved in one direction as they are spread apart so as to receive the end of a specimen, and as the jaw members are moved in the opposite direction, they approach each other to firmly grip the test specimen. Spring means act on the jaw members to urge them into the grip position. While the gripping device disclosed in my prior patent has many desirable features and advantages, it nevertheless suffers from certain disadvantages which the present invention is designed to overcome. One of these disadvantages is the need to execute a number of intricate and extensive machining operations to produce the housing used to operatively support various parts forming the gripping device and sustain the forces developed between the gripper jaws. The housing disclosed has a keystone configuration with outer side surfaces converging toward a lower end surface where the ends of the gripper jaws are exposed to receive a test piece between the jaws after they are separated. A deep hollowed-out portion in the front face of the housing essentially conforms to the keystone configuration of the housing itself so as to form inclined side walls for sliding engagement with the jaw members. The jaws each includes an inclined slot to receive a single cam member that is held in place by a cover plate. The cover plate is secured to a ledge positioned downwardly from the face surface of the housing. A deep chamfered edge was formed between the outer face surface of the housing and the face surface of the cover plate. The cover plate further includes two centrally-arranged slots, one extending to the upper end of the cover plate and the other extending to the lower end of the cover plate. The upper slot formed a guide for a pin extending from the cam member while the lower slot exposed the jaw members for observation during the clamping operation. The front and back face surfaces of the housing were each tapered into two directions by a laborious machine operation whereby the thickness of the housing increased from its top surface to a maximum thickness at about the top of the cavity in the housing and then decreased to a minimum thickness at the lower edge of the housing. The many maching operations required to produce such keystone-shaped housing with tapered front and back surfaces, as described, contribute materially to the cost of the gripping device. Moreover, the arrangement of parts limited the observation of the jaws during the gripping operation and rendered unnecessarily complicated the procedure required for replacing the gripper jaws.

Substantial amounts of metal must be removed from the housing in order to provide the required inclined side walls to support the jaw members for movement into and out of engagement with the end of a test piece. The amount of material removed from the housing, of course, reduces the maximum stress to which the gripping device may be subjected without breaking. The stresses are applied to the housing by a pull shaft. This shaft is secured by a threaded connection forming a first critical area in the housing which is the end opposite the end where the gripper jaws are exposed for receiving the test piece. There is, of course, a pull axis extending symmetrically through the gripping device. The housing to which the pull shaft is secured must be capable of withstanding the maximum stresses occurring during the actual testing procedure. At the same time, the housing is subjected to a stress produced by the separating force between the jaws. This represents a second critical area where the housing must resist maximum stresses.

SUMMARY OF THE INVENTION

It is an overall object of the present invention to provide an improved housing construction for a test piece gripping device as well as an improved construction and relationship of parts whereby the gripping device is capable of withstanding maximum stresses in an efficient and economical manner.

Another object of the present invention is to substantially reduce the multiplicity of intricate machining operations heretofore required for producing a housing for a test piece gripping device while at the same time maintaining or even increasing the strength of the housing.

It is a further object of the present invention to provide an improved faceplate and guide arrangement for a cam used to displace jaw members within a hollowed-out cavity in the housing of a test piece gripping device to facilitate both the replacement of the jaw members and improve visual observation at a site area where a test piece is inserted into a gap between the gripper jaws of the device.

The test piece gripping device of the invention comprises a housing having a test piece receiving end and an opposite end adapted for connection to a physical testing apparatus, the housing having longitudinal side pieces formed with parallel edge surfaces, the side pieces having coplanar front face surfaces terminated by a parallel and raised pad surface defined by a crosspiece connecting the side pieces at corresponding ends thereof, the housing including a wall extending between the side pieces and to the crosspiece while forming a back planar face surface parallel with the coplanar front face surfaces of the side pieces, the back planar face surface being terminated by a parallel and raised pad surface extending between the side pieces and to the test piece receiving end of the housing, the raised pad surfaces defining housing reinforcing ribs for maintaining an optimum pull axis along the housing by strengthening the housing at areas where it is subjected to maximum stresses occurring during an actual operation of the test piece gripping device, the longitudinal side pieces providing a pair of opposed wedging surfaces for sliding contact with jaw members having opposed face surfaces adapted to grip a test piece therebetween, the jaw members having coplanar outer face surfaces each of which defines a cam surface thereon which is inclined in a direction opposite the inclination of the wedging surface, a unitary cam member engaged with the cam surfaces, means projecting outwardly from the cam member for moving it longitudinally of the housing to effect simultaneous movement of the jaw members along the wedging surfaces, a faceplate secured to the housing in an overlying relation with the cam member and the jaw members, the faceplate having a longitudinal slot through which the means for moving the cam member extends, and resilient members between the jaw members and the crosspiece for urging the jaw members along the wedging surfaces provided by the housing.

The housing preferably includes recessed surfaces to support the faceplate along opposed edges of the side pieces with the exposed face surface of the faceplate being coplanar with the front face surfaces of the side pieces.

In the preferred form, the longitudinal slot formed in the faceplate extends continuously along the center of the faceplate from a point adjacent the upper terminal edge thereof to the lower terminal edge at the test piece receiving end of the housing whereby the longitudinal slot provides both guiding for the means used to move the cam member and exposure of part of the jaw members when in a clamped condition for visual observation thereof.

The means for moving the cam member preferably includes a guide block defining parallel guide surfaces with a height corresponding to the thickness of the faceplate. An outwardly projected portion of this guide block has a thickness substantially corresponding to the width of the slot in the faceplate.

These features and advantages of the present invention as well as others will be more fully understood when the following description is read in light of the accompanying drawings, in which:

FIG. 1 is a schematic front view of a physical testing apparatus provided with gripping devices of the present invention;

FIG. 2 is an isometric view of the gripping device of the present invention;

FIG. 3 is a sectional view taken along line III—III of FIG. 2; and

FIG. 4 is a plan view of a cam member forming part of the gripping device according to the present invention.

As schematically illustrated in FIG. 1, a physical testing apparatus 10 comprises vertical columns 12 and rails 14 which are supported by the vertical columns 12. Means, not shown, are provided for moving the rails 14 along the vertical columns 12 to change their position relative to one another. The physical testing apparatus 10 is provided with gripping devices 16 of the present invention, one connected to each of the rails 14 while gripping the opposite ends of a test specimen 18. Power components, schematically represented by the arrows 20, when activated, force the rails 14 and, hence, the gripping devices 16 away from each other to thereby subject the test specimen 18 to various tensile forces.

Referring now to FIGS. 2–4, each gripping device 16 has a test piece receiving end 21 and a connection end 22 adapted for connection to the rails 14 by a rod 23 having threaded ends. One threaded end of the rod 23 is passed into a trapped hole formed within the connection end 22 of the gripping device. The gripping device comprises, in general, a housing 24 which has an improved construction according to the present invention. The housing has a cavity in which resides a pair of jaw members 25 and spring members 25A urging the jaw members into a clamping or gripping relation at opposite sides of a workpiece between the jaw members. A faceplate 26 is secured by threaded fasteners 26A to the housing 24 in an overlying relation with the cavity therein. A cam member 27 engages both of the jaw members to move them longitudinally of the housing.

The housing 24 is formed from a single piece of metal and comprises a pair of longitudinal side pieces 30, a crosspiece 31 connected to the side pieces at corresponding ends thereof and a longitudinal wall 32 extending between the side pieces and to the crosspiece 31. The side pieces 30 have outer edge surfaces that are parallel with one another and coplanar front surfaces terminated by a parallel and raised pad surface 31A which is actually a thickened portion of the crosspiece 31. The longitudinal wall 32 forms a back planar face surface 32A that is parallel with the coplanar front surfaces of the side pieces 30. The back planar face surface is terminated by a parallel and raised pad surface 32B extending between the side pieces and to the test piece receiving end of the housing, as best shown in FIG. 3. An important feature of the present invention is the provision of the raised pad surfaces 31A and 32B which form reinforcing ribs for maintaining an optimum pull axis 33 which extends along the axis of rods 23 and then extend along the housing in a symmetrical manner both with respect to the thickness and width of the housing. In this respect, it will be observed in regard to FIG. 3 that because of the raised pad 31A, the metal added to the housing thereby enables the maintenance of an optimum pull axis along the housing which is midway along the opposed specimen engaging faces of gripper jaws 25. The raised pad surface 32B provides added metal to the back surface at the point of maximum stress upon the housing as a result of the separating force between the gripper jaws as a reaction force to the force necessary to grip a test piece between the jaws.

The side pieces 30 on their planar front faces have recessed surfaces 35 that lie below the planar front face of the side pieces by an amount corresponding to the thickness of cover plate 26 whereby the face surface of cover plate 26 and the face surfaces of the side pieces are coplanar. This greatly enhances the opportunity to visually observe the gripping of a test piece between the jaws 25 by forming an open space provided by an elongated slot 26B in the cover plate. This slot opens out of the lower end of the cover plate and extends to the opposite end of the cover plate where the slot terminates at a point adjacent the top edge thereof. The slot 26B is further used for guiding the squared pad raising above the top face surfaces of cam members 27. The pad 36 has a thickness corresponding to the thickness of cover plate 26. Projecting from the pad 36 is a rod 37 which has a thickness or diameter corresponding to the width of the pad. This permits the cover plate to be freely removed and replaced without additional loose parts otherwise required to provide guiding of the cam member along the cover plate. The rod 37 is received within an enlarged opening formed at one end of a lever 38 which is attached by a bolt 39 to the housing for pivotal movement. The lever has a handle 40. The handle extends along a straight line passing through the longitudinal center of the lever 38. It is preferred to provide a threaded connection between the handle 40 and the lever to advance and retract a locking pin into and out of engagement with a cam surface 41 machined into the side edge of the housing as best illustrated in FIG. 2.

In light of the foregoing description, it is apparent that the housing forming part of the test piece gripping device has a rectangular shape formed by parallel side surfaces that intersect at right angles with the planes of ends 21 and 22 which are parallel.

Although the invention has been shown in connection with a certain specific embodiment, it will be readily apparent to those skilled in the art that various changes in form and arrangement of parts may be made to suit requirements without departing from the spirit and scope of the invention.

I claim as my invention:

1. A test piece gripping device comprising a housing having a test piece receiving end and an opposite end adapted for connection to physical testing apparatus, said housing having longitudinal side pieces formed with parallel edge surfaces, said side pieces having coplanar front face surfaces terminated by a parallel and raised pad surface defined by a crosspiece connecting said side pieces at corresponding ends thereof, said housing including a wall extending between said side pieces and to said crosspiece while forming a back planar surface parallel with the coplanar front face surfaces of said side pieces, the back planar face surface being terminated by a parallel and raised pad surface extending between said side pieces and to the test piece receiving end of the housing, said raised pad surfaces defining housing reinforcing ribs for maintaining an optimum pull axis along the housing, said longitudinal side pieces providing a pair of opposed wedging surfaces which converge away from said crosspiece, a pair of jaw members slideable over said wedging surfaces and including opposed faces adapted to grip a test piece therebetween along said pull axis, said jaw members having coplanar outer faces, each of said coplanar faces terminating a cam surface which is inclined in a direction opposite the inclination of the wedging surface with which each of said jaw members is engaged, a unitary cam member engaged with said cam surfaces, means projecting outwardly of said cam member for moving the cam member longitudinally of said housing to effect simultaneous movement of said jaw members along said wedging surfaces and hence into a spaced-apart condition for receiving a test piece therebetween, a faceplate secured to said housing and overlying said cam member and said jaw members, said faceplate having a longitudinal slot through which said means extend, and resilient members interposed between said jaw members and said crosspiece for urging said jaw members along said wedging surfaces into a clamping condition.

2. The test piece gripping device according to claim 1 wherein the side pieces of said housing include recessed surfaces to support said faceplate along opposed edges thereof with the exposed face surface of said faceplate being coplanar with the front face surfaces of said side pieces.

3. The test piece gripping device according to claim 2 wherein said recessed surfaces in the side pieces extend parallel with said edge surfaces of the side pieces.

4. The test piece gripping device according to claim 1 further including a lever coupled at one end thereof to the projected end of said means, a shaft carried by said housing to pivotally support said lever.

5. The test piece gripping device according to claim 1 wherein said longitudinal slot extends continuously along the center of said faceplate from a point adjacent the upper terminal edge to the lower terminal edge at the test piece receiving end of said housing to both guide said means and expose part of said jaw members in a clamped condition for visual observation.

6. The test piece gripping device according to claim 1 wherein said housing has a rectangular shape defined by two opposed parallel edge surfaces intersecting at right angles.

7. The test piece gripping device according to claim 1 wherein said means includes a pad defining parallel guide surfaces with a height corresponding to the thickness of said faceplate, the projected portion of said means extending outwardly of said guide block has a thickness substantially corresponding to the width of the slot in said faceplate.

8. The test piece gripping device according to claim 1 wherein each of said raised pad surfaces extends to the parallel edge surfaces of said side pieces.

* * * * *